United States Patent [19]

Kikumoto et al.

[11] Patent Number: 4,562,211

[45] Date of Patent: * Dec. 31, 1985

[54] PHARMACEUTICALLY ACTIVE 2-SUBSTITUTED-1-(OMEGA-AMINOALKOXY)BENZENES

[75] Inventors: Ryoji Kikumoto, Machida; Akihiro Tobe, Kawasaki; Shinji Tonomura, Tokyo; Hidenobu Ikoma, Kawasaki, all of Japan

[73] Assignee: Mitsubishi Chemical Industries, Ltd., Tokyo, Japan

[ * ] Notice: The portion of the term of this patent subsequent to May 17, 1994 has been disclaimed.

[21] Appl. No.: 94,762

[22] Filed: Nov. 16, 1979

Related U.S. Application Data

[63] Continuation of Ser. No. 853,743, Nov. 21, 1977, abandoned.

[30] Foreign Application Priority Data

Dec. 6, 1976 [JP] Japan ............................... 51-146254
Dec. 17, 1976 [JP] Japan ............................... 51-151632

[51] Int. Cl.$^4$ .................. A61K 31/135; A61K 31/205
[52] U.S. Cl. .................................... 514/648; 514/157; 514/210; 514/211; 514/227; 514/228; 514/255; 514/554; 514/555; 514/651
[58] Field of Search ..................... 260/570, 570.7; 424/316, 330; 514/157, 210, 211, 227, 228, 255, 554, 555, 648, 651

[56] References Cited

U.S. PATENT DOCUMENTS

| 2,534,236 | 12/1950 | Cusic | 260/253 |
| 2,703,324 | 3/1955 | Binkley | 260/570 X |
| 2,768,207 | 10/1956 | Cheney et al. | 260/570 |
| 2,966,518 | 12/1960 | Johnson | 260/570.7 X |
| 4,024,282 | 5/1977 | Kikumoto et al. | 260/570 X |
| 4,060,641 | 11/1977 | Kikumoto et al. | 260/570 X |

FOREIGN PATENT DOCUMENTS

| 45-9937 | 4/1970 | Japan | 260/570.7 |
| 45-9938 | 4/1970 | Japan | 260/570.7 |

OTHER PUBLICATIONS

Rubinstein et al., "Jour. Med. Chem.", vol. 9, pp. 804-809 (1966).
Cheney et al. (II), "J.A.C.S.", vol. 71, pp. 60-64 (1949).
Wheatley et al., "J.A.C.S.", vol. 71, pp. 64-66 (1949).
Protiva et al., "Chemical Abstracts", vol. 1, p. 577 (1951).
Toyoshima et al. (III) and (IV), "Yakugaku Zasshi", vol. 89, pp. 1078-1084, 1417-1425, (1969).
Schuler, "Molecular Modification in Drug Design", Advances in Chemistry, No. 45, pp. 114-115 and 129-136 (1964).
Benson et al., "Tranquilizing and Antidepressant Drugs", pp. 27 and 30 (1962).

*Primary Examiner*—Robert V. Hines
*Attorney, Agent, or Firm*—Oblon, Fisher, Spivak, McClelland & Maier

[57] ABSTRACT

2-Substituted-1-(omega-aminoalkoxy)benzenes are prepared and found useful as pharmaceutical agents, particularly as antidepressants.

15 Claims, No Drawings

PHARMACEUTICALLY ACTIVE 2-SUBSTITUTED-1-(OMEGA-AMINOALKOXY)-BENZENES

This is a continuation of application Ser. No. 853,743, filed Nov. 21, 1977, and now abandoned.

BACKGROUND OF THE INVENTION

1. Field of the Invention

This invention relates to 2-substituted-1-(omega-aminoalkoxy)benzenes which are pharmacologically active as antidepressants.

2. Description of the Prior Art

L. C. Cheney et al, J. Am. Chem. Soc., Vol. 71, 60–64 (1949) describes several diphenylmethanes containing a substituent at the 2-position, including 2-dimethylaminoethoxy, 2-diethylaminoethoxy, 2-morpholinoethoxy, 2-(1-piperidyl)ethoxy, 2-isopropylaminoethoxy, 3-(1-piperidyl)propoxy, 3-dimethylaminopropoxy and 3-dibutylaminopropoxy.

That reference also indicates that 2-(2-aminoethoxy)diphenylmethanes and 2-(3-aminopropoxy)diphenylmethanes have antihistaminic and local anesthetic activity in animals. Similarly, U.S. Pat. Nos. 2,703,324, 2,966,518, 2,534,236 and 2,768,207 disclose 2-omega-aminoalkoxydiphenylmethanes such as 2-(3-diethylaminopropyl)diphenylmethane and 2-(5-dimethylaminopentyl)diphenylmethane. J. Med. Chem., Vol. 9, page 806 (1966) discloses 2-(4-dimethylaminobutoxy)diphenylmethane.

Journal Pharm. Soc. Japan, Vol. 89, pages 1078–1084 (1969) and Vol. 89, pages 1417–1425 (1970), Japanese Patents published for opposition Nos. 9937/1970 and 9938/1970 disclose 2-(omega-dialkylaminoethoxy)diphenyl ethers, 2-(omega-cycloiminoethoxy)diphenyl ethers, 2-(omega-dialkylaminopropoxy)diphenyl ethers and 2-(omega-cycloiminopropoxy)diphenyl ethers, each benzene ring being optionally substituted by chloro or methyl.

Chemical Abstracts, Vol. 72, 3152 y and Vol. 73, P 76852 disclose 2-(3-diethylaminopropoxy)diphenyl ether.

Chemical Abstracts, Vol. 45, page 577 (1951) discloses 2-(diethylaminoethoxy)diphenyl sulfide.

U.S. Pat. No. 2,703,324 discloses 2-(2-diethylaminoethoxy)diphenylmethylmethane.

U.S. Pat. Nos. 2,187,723 and 3,213,140 disclose 2-omega-aminoalkoxybiphenyl such as 2-(2-pentylaminoethoxy)biphenyl. Similarly, British Pat. No. 521,575 discloses 2-omega-aminoalkoxybiphenyl such as 2-(3-dimethylaminopropoxy)biphenyl, 2-(2-aminoethoxy)biphenyl and 2-(2-ethylaminoethoxy)biphenyl. However, none of these prior art compounds is disclosed as having antidepressant activity.

SUMMARY OF THE INVENTION

Accordingly, it is an object of this invention to provide novel 2-substituted-1-(omega-aminoalkoxy)benzenes having superior antidepressant activity.

This and other objects of the present invention as will hereinafter become clear have been attained by providing compounds of the formula (I):

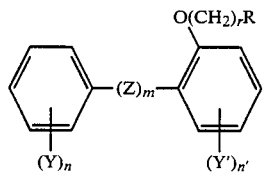

(I)

wherein R is (1)

wherein $R_1$ and $R_2$ which are alike or different are selected from the group consisting of hydrogen, $C_1$–$C_5$ alkyl and $C_1$–$C_5$ hydroxyalkyl or (2) $C_3$–$C_7$ N,N-polymethyleneiminyl, morpholino, thiomorpholino, 4-oxothiomorpholino, 1-piperazinyl, 4-methyl-1-piperazinyl, 4-ethyl-1-piperazinyl or 4-acetyl-1-piperazinyl; Y and Y' which are alike or different are selected from the group consisting of hydrogen, halo, hydroxy, trifluoromethyl, $C_1$–$C_5$ alkyl or $C_1$–$C_5$ alkoxy with the proviso that both Y and Y' are not hydrogen; Z is oxy, thio, methylene, monosubstituted methylene

wherein $R_3$ is $C_1$–$C_5$ alkyl, or disubstituted methylene

wherein $R_4$ and $R_5$ are $C_1$–$C_5$ alkyl; r is an integer of 3, 4 or 5; m is an integer of 0 or 1; n is an integer of 1 to 5; and n' is an integer of 1 to 4, with the proviso that when r is 3 R is $C_1$–$C_5$ alkylamino, and the acid addition salts thereof.

This invention also relates to a method for palliating conditions of depression in warm-blooded animals which comprises administering to said animal an antidepressant effective amount of a compound of the formula (II):

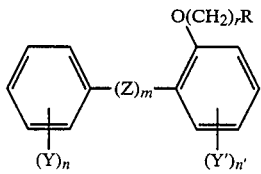

(II)

wherein R is (1)

wherein $R_1$ and $R_2$ which are alike or different are selected from the group consisting of hydrogen, $C_1$–$C_5$ alkyl and $C_1$–$C_5$ hydroxyalkyl or (2) $C_3$–$C_7$ N,N-polymethyleneiminyl, morpholino, thiomorpholino, 4-oxothiomorpholino, 1-piperazinyl, 4-methyl-1-piperazinyl, 4-ethyl-1-piperazinyl or 4-acetyl-1-piperazinyl; Y and Y' which are alike or different are selected from the group consisting of hydrogen, halo, hydroxy, trifluoromethyl, $C_1$–$C_5$ alkyl or $C_1$–$C_5$ alkoxy with the proviso that both Y and Y' are not hydrogen; Z is oxy, thio, methylene, monosubstituted methylen

wherein $R_3$ is $C_1$–$C_5$ alkyl, or disubstituted methylene

wherein $R_4$ and $R_5$ are $C_1$–$C_5$ alkyl; r is an integer of 3, 4 or 5; m is an integer of 0 or 1; n is an integer of 1 to 5; and n' is an integer of 1 to 4, or the acid addition salts thereof.

Furthermore, this invention relates to a method for producing the compound of the formula (I) or (II) which comprises reacting an 2-substituted-1-(omega-halogenoalkoxy)benzene of the formula (III):

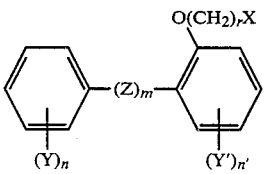 (III)

wherein X is halogen; and Y, Y', Z, r, m, n and n' are as defined in the formula (I) or (II), with an amine having the formula (IV):

R—H  (IV)

wherein R is as defined in the formula (I) or (II).

DESCRIPTION OF THE PREFERRED EMBODIMENTS

As summarized above, this invention relates to a group of compounds useful as pharmaceutical agents, which compounds are represented by the formula (I) or (II):

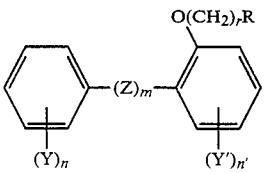 (I) or (II)

wherein R is (1)

wherein $R_1$ and $R_2$ which are alike or different are selected from the group consisting of hydrogen; $C_1$–$C_5$ alkyl such as methyl, ethyl, propy, isopropyl, butyl, isobutyl or the like; and $C_1$–$C_5$ hydroxyalkyl such as hydroxymethyl, 1-hydroxyethyl, 2-hydroxyethyl, 1-hydroxypropyl, 2-hydroxypropyl, 3-hydroxypropyl or the like or (2) $C_3$–$C_7$ N,N-polymethyleneiminyl such as 1-azetidinyl, 1-pyrrolidinyl, piperidino or 1-hexamethyleneiminyl, morpholino, thiomorpholino, 4-oxothiomorpholino, 1-piperazinyl, 4-methyl-1-piperazinyl, 4-ethyl-1-piperazinyl, or 4-acetyl-1-piperazinyl; Y and Y' which are alike or different are selected from the group consisting of hydrogen, halo such as fluoro, chloro or bromo, hydroxy, trifluoromethyl, $C_1$–$C_5$ alkyl such as methyl, ethyl, propyl, isopropyl or the like, or $C_1$–$C_5$ alkoxy such as methoxy, ethoxy, propoxy, isopropoxy or the like, with the proviso that both Y and Y' are not hydrogen; Z is oxy, thio, methylene, monosubstituted methylene

wherein $R_3$ is $C_1$–$C_5$ alkyl such as methyl, ethyl, propyl or the like, or disubstituted methylene

wherein $R_4$ and $R_5$ are $C_1$–$C_5$ alkyl such as methyl, ethyl, propyl or the like; r is an integer of 3, 4 or 5; m is an integer of 0 or 1; n is an integer of 1 to 5 (preferably 1 or 2); n' is an integer of 1 to 5 (preferably 1 or 2); and, in case of formula (I), with the proviso that when r is 3 R is $C_1$–$C_5$ alkylamino.

Suitable examples of R in formula (I) or (II) include amino, $C_1$–$C_3$ alkylamino such as methylamino and ethylamino, $C_2$–$C_6$ dialkylamino such as dimethylamino, diethylamino or the like, $C_1$–$C_3$ hydroxyalkylamino, $C_2$–$C_6$ bis(hydroxyalkyl)amino such as bis(2-hydroxyethyl)amino, $C_2$–$C_6$ N-alkyl-N-hydroxyalkylamino and 1-pyrrolidinyl.

Suitable examples of Y and Y' in formula (I) or (II) include hydrogen, halo such as chloro, hydroxy, trifluoromethyl, $C_1$–$C_3$ alkyl such as methyl, and $C_1$–$C_3$ alkoxy such as methoxy and ethoxy.

Y can be substituted at any of 2', 3', 4', 5' and 6'-position. Similarly, Y' can be substituted at any of 3, 4, 5 and 6-position.

Suitable examples of Z in formula (I) or (II) include oxy, thio, methylene and methylmethylene.

The preferred R in formula (I) or (II) includes methylamino, ethylamino, dimethylamino, diethylamino, bis(2-hydroxyethyl)amino and 1-pyrrolidinyl.

The preferred Y and Y' in formula (I) or (II) are selected from the group consisting of hydrogen, chloro, hydroxy, methyl, methoxy and ethoxy.

The preferred Z in formula (I) or (II) includes oxy and methylene.

The preferred r is 3 or 4.

The pharmaceutically acceptable acid addition salts of the above compounds are, of course, also included within the scope of this invention.

It will be understood that the term "pharmaceutically acceptable acid addition salts" as used herein is intended to include non-toxic salts of the compounds of this invention with an anion. Representative of such salts are hydrochlorides, hydrobromides, sulfates, phosphates, nitrates, acetates, succinates, adipates, propionates, tartrates, maleates, citrates, benzoates, toluenesulfonates, and methanesulfonates.

Of the compounds of this invention, it will be understood that the following compounds are preferred.
2-(4-methylaminobutoxy)-3-methyldiphenylmethane
2-(4-dimethylaminobutoxy)-3-methyldiphenylmethane
2-(4-dimethylaminobutoxy)-5-methyldiphenylmethane
2-(4-methylaminobutoxy)-4'-methyldiphenylmethane
2-(4-methylaminobutoxy)-4'-chlorodiphenylmethane
2-[4-bis(2-hydroxyethyl)aminobutoxy]-4'-methoxydiphenylmethane
2-(4-methylaminobutoxy)-2'-methoxydiphenylmethane
2-(4-methylaminobutoxy)-2'-hydroxydiphenylmethane
2-(4-dimethylaminobutoxy)-2'-hydroxydiphenylmethane
2-(4-methylaminobutoxy)-2'-ethoxydiphenyl ether
2-(4-methylaminobutoxy)-2'-methyldiphenyl ether
2-(3-methylaminopropoxy)-2'-methyldiphenyl ether
2-(3-dimethylaminopropoxy)-2'-methyldiphenyl ether
2-(3-ethylaminopropoxy)-2'-methyldiphenyl ether
2-(3-diethylaminopropoxy)-2'-methyldiphenyl ether
2-[3-(1-pyrrolidinyl)propoxy]-2'-methyldiphenyl ether Of the compounds of this invention, it will be understood that the following compounds are most preferred due to their high level of antidepressant activity and their low level of toxicity.
2-(4-methylaminobutoxy)-3-methyldiphenylmethane
2-(4-dimethylaminobutoxy)-3-methyldiphenylmethane
2-(4-dimethylaminobutoxy)-5-methyldiphenylmethane
2-(4-methylaminobutoxy)-2'-methoxydiphenylmethane
2-(4-methylaminobutoxy)-2'-hydroxydiphenylmethane
2-(4-dimethylaminobutoxy)-2'-hydroxydiphenylmethane
2-(4-methylaminobutoxy)-2'-ethoxydiphenyl ether
2-(4-methylaminobutoxy)-2'-methyldiphenyl ether
2-(3-methylaminopropoxy)-2'-methyldiphenyl ether
2-(3-dimethylaminopropoxy)-2'-methyldiphenyl ether

PREPARATION

The compounds of this invention are prepared by reacting a 2-substituted-1-(omega-halogenoalkoxy)benzene of the formula (III):

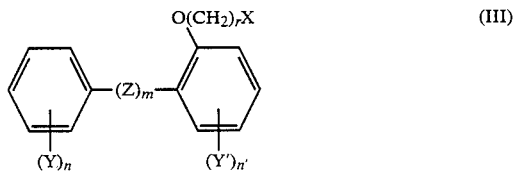

wherein X is halogen; and Y, Y', Z, r, m, n and n' are as defined in the formula (I) or (II), with an amine having the formula (IV):

R—H       (IV)

wherein R is as defined in the formula (I) or (II).

The 2-substituted-1-(omega-halogenoalkoxy)benzene starting materials can be prepared by reacting a 2-substituted phenol having the formula (V):

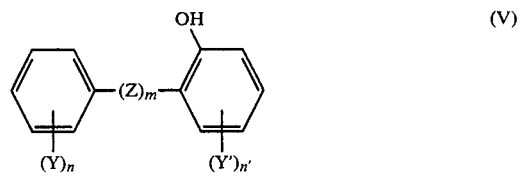

wherein Y, Y', Z, n, n' and m are as defined in the formula (I) or (II), with a 1,3-dihalogenopropane, 1,4-dihalogenobutane or 1,5-dihalogenopentane in the presence of an alkali.

Suitable examples of 2-substituted phenols having the formula (V) include 2-hydroxy-3-methyldiphenylmethane, 2-hydroxy-5-methyldiphenylmethane, 2-hydroxy-4'-methyldiphenylmethane, 2-hydroxy-5-chlorodiphenylmethane, 2-hydroxy-4'-chlorodiphenylmethane, 2-hydroxy-4'-methoxydiphenylmethane, 2-hydroxy-2'-methoxydiphenylmethane, 2,2'-dihydroxydiphenylmethane, 2,2'-dihydroxybiphenyl, 2,2'-dihydroxydiphenyl ether, 2-hydroxy-2'-methoxydiphenyl ether, 2-hydroxy-2'-ethoxydiphenyl ether, 2-hydroxy-2'-methyldiphenyl ether, 2-hydroxy-3,5-dimethyl-2',3'-dimethoxydiphenylmethane, 2-hydroxy-3-methyl-5,4'-dichlorodiphenylmethane, 2-hydroxy-5-chloro-3-isopropyl-6-methyldiphenylmethane, 2-hydroxy-4,6-dimethyl-4'-bromodiphenylmethane, 2-hydroxy-4'-chlorodiphenyl ether, 2-hydroxy-3,4'-dimethyldiphenyl ether, 2-hydroxy-3,5-dibromobiphenyl, 2-hydroxy-3,5,4'-tribromobiphenyl, 2-hydroxy-3,5-dimethylbiphenyl, 2-hydroxy-3-ethylbiphenyl and the like.

The amine reacts with the equimolecular amount of the 2-substituted-1-(omega-halogenoalkoxy)benzene. However, the use of the excess amine accelerates the reaction. Normally, the amount of the amine to be employed is in the range of 1 to 100 moles, preferably 2 to 40 moles per mole of the 2-substituted-1-(omega-halogenoalkoxy)benzene. A large amount of the amine serves also as a solvent.

The reaction can be carried out without an added solvent. However, the use of a reaction-inert solvent makes a homogeneous reaction possible.

Examples of such solvents are water, dioxane, tetrahydrofuran, dimethyl sulfoxide, lower aliphatic alcohols and the mixture thereof. The preferred solvent is water-lower aliphatic alcohol.

The reaction temperature is not critical, but normally ranges from room temperatures to 150° C., preferably from room temperature to 100° C.

The reaction time varies widely with the reaction temperature and the reactivity of the starting materials, but normally is in the range of from 10 minutes to 40 hours.

The presence of bases which neutralize a hydrogen halide formed in the course of the reaction accelerates the reaction. Examples of such bases are inorganic bases such as potassium hydroxide, sodium hydroxide, potassium carbonate, sodium carbonate and the like; and tertiary amines such as pyridine, triethylamine and the like.

The amount of the base to be employed is normally in the range of 1 to 5 moles per mole of the 2-substituted-1-(omega-halogenoalkoxy)benzene.

When the base is absent, the 2-substituted-1-(omega-aminoalkoxy)benzenes react with a hydrogen halide formed during the reaction, and are converted to the acid addition salts thereof.

Acid addition salts of the 2-substituted-1-(omega-aminoalkoxy)benzenes may be conveniently prepared by contacting the compounds with a suitable acid.

The 2-substituted-1-(omega-aminoalkoxy)benzenes and the acid addition salts thereof may be purified by recrystallization employing a suitable solvent such as alcohol-ether. Pharmacological testing of the 2-substituted-1-(omega-aminoalkoxy)benzenes has demonstrated that they are useful as antidepressant agents as evidenced by their ability to reverse reserpine hypothermia in mice.

The compounds have been tested in mice for antidepressant, sedative, anticonvulsant and anticholinergic activity. The compounds were administered intraperitoneally and the activities of the compounds were compared with those of Amitriptyline.

Antidepresssant activity was evaluated by antagonism of reserpine (5 mg/kg i.p.) induced hypothermia (P. S. J. Spencer in "Antidepressant Drugs" S. Garattini and M. N. G. Duhes, ed., Excerpta Medica Foundation, Amsterdam, pages 194–204 (1967)) and antireserpine activity was expressed as relative potency (Amitriptyline=1).

LD50 was calculated by Litchfield-Wilcoxon method.

CNS depressant activity was defined by the ability of the compounds to cause neurological deficit as measured by traction test (S. Courvoisier, R. Ducrot, L. Julou; "Psychotropic Drugs" ed. by S. Garattini, V. Ghetti, page 373, (1957)) and spontaneous motor activity (Spontaneous motor activity was measured by ANIMEX apparatus).

Anticonvulsant activity was determined by antagonism of electroshock induced tonic extensor (L. S. Goodman, M. Singh Grewak, W. C. Brown and E. A. Swinyard, J. Pharmacol, Exptal. Therap., 108, 168 (1953)).

Central anticholinergic effect was assessed by testing the tremorine induced tremor in mice (G. M. Everett, L. E. Bloucus and J. M. Sheppard, Science 124 79 (1956)).

Results are summarized in Table I and Table II, in which ED50 is defined as the dose of the test compounds, which prevent 50% of each response.

TABLE 1

Antireserpine Activity in Mice

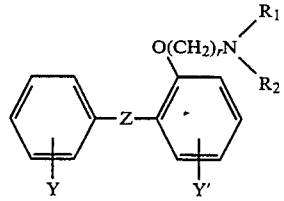

| No. | Y' | Y | $R_1$ | $R_2$ | Z | r | Addition moiety | Relative Potency | LD$_{50}$ (mg/kg i.p.) |
|---|---|---|---|---|---|---|---|---|---|
| 1 | 3-CH$_3$ | H | CH$_3$ | H | —CH$_2$— | 4 | HCl | 0.56 | 500–700 |
| 2 | 3-CH$_3$ | H | CH$_3$ | CH$_3$ | —CH$_2$— | 4 | HCl | 0.66 | 500–700 |
| 3 | 5-CH$_3$ | H | CH$_3$ | CH$_3$ | —CH$_2$— | 4 | HCl | 0.70 | 500–700 |
| 4 | H | 4'-CH$_3$ | CH$_3$ | H | —CH$_2$— | 4 | HCl | 0.44 | |
| 5 | H | 4'-Cl | CH$_3$ | H | —CH$_2$— | 4 | HCl | 0.44 | |
| 6 | H | 4'-OCH$_3$ | CH$_2$CH$_2$OH | CH$_2$CH$_2$OH | —CH$_2$— | 4 | HCl | 0.44 | |
| 7 | H | 2'-OCH$_3$ | CH$_3$ | H | —CH$_2$— | 4 | HCl | 0.85 | 600 |
| 8 | H | 2'-OH | CH$_3$ | H | —CH$_2$— | 4 | HCl | 1.00 | 600–700 |
| 9 | H | 2'-OH | CH$_3$ | CH$_3$ | —CH$_2$— | 4 | HCl | 0.77 | |
| 10 | H | 2'-OC$_2$H$_5$ | CH$_3$ | H | —O— | 4 | (COOH)$_2$ | 0.90 | |
| 11 | H | 2'-CH$_3$ | CH$_3$ | H | —O— | 4 | HCl | 0.65 | |
| 12 | H | 2'-CH$_3$ | CH$_3$ | H | —O— | 3 | HCl | 1.12 | |
| 13 | H | 2'-CH$_3$ | CH$_3$ | CH$_3$ | —O— | 3 | HCl | 0.95 | |
| 14 | H | 2'-CH$_3$ | C$_2$H$_5$ | H | —O— | 3 | HCl | 0.46 | |
| 15 | H | 2'-CH$_3$ | C$_2$H$_5$ | C$_2$H$_5$ | —O— | 3 | HCl | 0.44 | |
| 16 | H | 2'-CH$_3$ | —CH$_2$CH$_2$CH$_2$CH$_2$— | | —O— | 3 | HCl | 0.42 | |
| 17 | Amitriptyline | | | | | | | 1.00 | 300 |

TABLE II

CNS Depressant, Anticonvulsant and Central Anticholinergic Activity in Mice

| Compound | Anti-Convulsant Activity ED50 (mg/kg p.o.) | Muscle Relaxant Action ED50 (mg/kg p.o.) | Spontaneous Motor Activity Depression ED50 (mg/kg p.o.) | Antitremorine Effect ED50 (mg/kg p.o.) |
|---|---|---|---|---|
| 2-(4-methylaminobutoxy)-2'-hydroxydiphenyl-methane hydrochloride | 190 | 390 | 175 | >>200 |
| Amitriptyline | 19 | 40 | 28 | 11 |

It will be apparent from Tables I and II that the 2-substituted-1-(omega-aminoalkoxy)benzenes exhibit antireserpine activity and comparable to that of Amitriptyline, while they exhibit low toxicity, weak CNS depressant and anticholinergic action.

The compounds of this invention can be administered by any means that effects palliating conditions of depression in warm-blooded animals.

For example, administration can be parenterally, subcutaneously, intravenously, intramuscularly, or intraperitoneally. Alternatively or concurrently, administration can be by the oral route. The dosage administered will be dependent upon the age, health and weight of the recipient, the extent of depression, kind of concurrent treatment if any, frequency of treatment, and the nature of the effect desired. Generally, a daily dosage of the active ingredient compound will be from about 0.5 to 50 mg per kg of body weight. Normally, from 1 to 30 mg per kg per day, in one or more applications per day is effective to obtain the desired result.

The compound of Formula I can be employed in dosage forms such as tablets, capsules, powder packets, or liquid solutions, suspension, or elixirs, for oral administration, or sterile liquid formulations such as solutions or suspensions for parenteral use. In such compositions, the active ingredient will ordinarily always be present in an amount of at least 0.5% by weight based on the total weight of the composition and not more than 90% by weight.

Besides the active ingredient of this invention, the composition will contain a solid or liquid non-toxic pharmaceutical carrier for the active ingredient. In one embodiment of a composition, the solid carrier can be a capsule of the ordinary gelatin type. In the capsule will be from about 30–60% by weight of a compound of Formula I and 70–40% of a carrier. In another embodiment, the active ingredient can be tableted with or without adjuvants, or put into powder packets. These capsules, tablets and powders will generally constitute from about 5% to about 95% and preferably from 25% to 90% by weight of the active ingredient. These dosage forms preferably contain from about 5 to about 500 mg of active ingredients, with from about 25 to about 250 mg being most preferred.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as propylene glycol and polyethylene glycol are preferred liquid carriers, particularly for injectible solutions such as saline will ordinarily contain from about 0.5% to 20% and preferably about 1 to 10% by weight of the active ingredient.

As mentioned above, oral administration can be in a suitable suspension or syrup, in which the active ingredient normally will constitute from about 0.5 to 10% by weight.

The pharmaceutical carrier in such composition can be a watery vehicle such as an aromatic water, a syrup or a pharmaceutical mucilage.

The following examples are presented to further illustrate the preparation of the compounds of this invention.

EXAMPLE 1

A solution of 5.0 g of 2-(4-bromobutoxy)-3-methyldiphenylmethane, 20 ml of 40% methylamine aqueous solution, and 100 ml of ethanol is allowed to stand at room temperature for 8 hours. Ethanol and excess methylamine are distilled in vacuo, 2N—NaOH aqueous solution is added, and the reaction product is extracted with ether. The ether solution is distilled, 2N—HCl solution is added and the solution is evaporated to dryness.

The residue is recrystallized from ethanol-ether to give 4.1 g (85% yield) of 2-(4-methylaminobutoxy)-3-methyldiphenylmethane hydrochloride, m.p. 94°–98° C.

Analysis—Calcd. for $C_{19}H_{25}NO \cdot HCl$ (percent): C, 71.34; H, 8.19; N, 4.38. Found (percent): C, 71.05; H, 8.23; N, 4.28.

EXAMPLE 2

A solution of 5.0 g of 2-(4-bromobutoxy)-4'-methoxydiphenylmethane in 10 g of diethanolamine is allowed to stand at room temperature for 10 hours.

Diethanolamine is evaporated in vacuo, 2N—NaOH aqueous solution is added, and the reaction product is extracted with ether. The ether solution is distilled, 2N—HCl solution is added, and the solution is evaporated to dryness. The residue is recrystallized from ethanol-ether to give 4.0 g (69% yield) of 2-[4-bis(2-hydroxyethyl)aminobutoxy]-4'-methoxydiphenylmethane hydrochloride, m.p. 102°–104° C.

Analysis—Calcd. for $C_{22}H_{31}O_4N \cdot HCl$ (percent): C, 64.45; H, 7.87; N, 3.42. Found (percent): C, 64.55; H, 7.86; N, 3.37.

The compounds in the following table were prepared according to the procedure described in Example 1 or 2 using the appropriate starting materials.

Results are summarized in Table III.

TABLE III

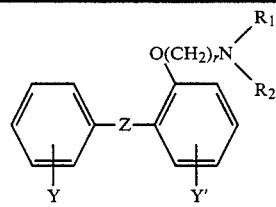

| No. | Y' | Y | $R_1$ | $R_2$ | Z | r | Addition moiety | Preparation Process (Ex. No.) | m.p. (°C.) | Analysis Upper: Calcd. Lower: Found C | H | N |
|---|---|---|---|---|---|---|---|---|---|---|---|---|
| 1 | 3-CH$_3$ | H | CH$_3$ | H | —CH$_2$— | 4 | HCl | 1 | 94–96 | 71.34 | 8.19 | 4.38 |
|   |   |   |   |   |   |   |   |   |   | 71.05 | 8.23 | 4.28 |
| 2 | 3-CH$_3$ | H | CH$_3$ | CH$_3$ | —CH$_2$— | 4 | HCl | 1 | 152–157 | 71.94 | 8.45 | 4.20 |
|   |   |   |   |   |   |   |   |   |   | 72.07 | 8.32 | 4.19 |
| 3 | 5-CH$_3$ | H | CH$_3$ | H | —CH$_2$— | 4 | HCl | 1 | 152–156 | 71.34 | 8.19 | 4.38 |
|   |   |   |   |   |   |   |   |   |   | 71.36 | 8.16 | 4.15 |
| 4 | 5-CH$_3$ | H | CH$_3$ | CH$_3$ | —CH$_2$— | 4 | HCl | 1 | 93–98 | 71.94 | 8.45 | 4.20 |
|   |   |   |   |   |   |   |   |   |   | 71.64 | 8.48 | 3.90 |
| 5 | H | 4'-CH$_3$ | CH$_3$ | H | —CH$_2$— | 4 | HCl | 1 | 90–92 | 71.34 | 8.19 | 4.38 |

TABLE III-continued

| No. | Y' | Y | R₁ | R₂ | Z | r | Addition moiety | Preparation Process (Ex. No.) | m.p. (°C.) | Analysis Upper: Calcd. Lower: Found C | H | N |
|---|---|---|---|---|---|---|---|---|---|---|---|---|
| 6 | H | 4'-CH₃ | CH₃ | CH₃ | —CH₂— | 4 | HCl | 1 | 138–140 | 71.09 / 71.94 | 8.45 / 8.45 | 4.11 / 4.20 |
| 7 | 5-Cl | H | CH₃ | H | —CH₂— | 4 | HCl | 1 | 149–153 | 71.82 / 63.53 / 63.79 | 8.66 / 6.81 / 6.97 | 4.03 / 4.17 / 3.99 |
| 8 | 5-Cl | H | CH₃ | CH₃ | —CH₂— | 4 | HCl | 1 | 117–121 | 64.40 / 64.22 | 7.11 / 7.24 | 3.95 / 3.82 |
| 9 | H | 4'-Cl | CH₃ | H | —CH₂— | 4 | HCl | 1 | 113–114.5 | 63.53 / 63.68 | 6.81 / 7.11 | 4.17 / 4.12 |
| 10 | H | 4'-Cl | CH₃ | CH₃ | —CH₂— | 4 | HCl | 1 | 127.5–129.5 | 64.40 / 64.70 | 7.11 / 7.23 | 3.95 / 3.78 |
| 11 | H | 4'-OCH₃ | CH₃ | H | —CH₂— | 4 | HCl | 1 | 96–98 | 67.94 / 67.72 | 7.80 / 7.98 | 4.17 / 4.07 |
| 12 | H | 4'-OCH₃ | CH₃ | CH₃ | —CH₂— | 4 | HCl | 1 | 140–143 | 68.65 / 68.37 | 8.07 / 8.25 | 4.00 / 3.92 |
| 13 | H | 4'-OCH₃ | —CH₂CH₂CH₂CH₂— | | —CH₂— | 4 | HCl | 2 | powder | 70.28 / 70.00 | 8.04 / 8.24 | 3.73 / 4.00 |
| 14 | H | 4'-OCH₃ | CH₂CH₂OH | CH₂CH₂OH | —CH₂— | 4 | HCl | 2 | 102–104 | 64.45 / 64.55 | 7.87 / 7.86 | 3.42 / 3.37 |
| 15 | H | 2'-OCH₃ | CH₃ | H | —CH₂— | 4 | HCl | 1 | 133–141.5 | 67.94 / 68.12 | 7.80 / 7.80 | 4.17 / 4.20 |
| 16 | H | 2'-OH | CH₃ | H | —CH₂— | 4 | HCl | 1 | 139–142 | 67.38 / 67.38 | 7.22 / 7.48 | 4.37 / 4.83 |
| 17 | H | 2'-OH | CH₃ | CH₃ | —CH₂— | 4 | HCl | 1 | 156–160 | 67.94 / 67.71 | 7.80 / 7.80 | 4.17 / 4.05 |
| 18 | H | 2'-OH | CH₃ | H | — | 4 | HCl | 1 | 151–156 | 67.17 / 66.36 | 7.52 / 7.54 | 4.35 / 4.28 |
| 19 | H | 2'-OH | CH₃ | H | —O— | 4 | HCl | 1 | 133–134.5 | 63.06 / 63.01 | 6.85 / 6.92 | 4.33 / 4.50 |
| 20 | H | 2'-OH | CH₃ | CH₃ | —O— | 4 | HCl | 1 | 124–125 | 63.99 / 64.10 | 7.16 / 7.13 | 4.15 / 4.09 |
| 21 | H | 2'-OCH₃ | CH₃ | H | —O— | 4 | (COOH)₂ | 1 | 146-8 | 61.37 / 61.29 | 6.44 / 6.32 | 3.58 / 3.60 |
| 22 | H | 2'-OC₂H₅ | CH₃ | H | —O— | 4 | (COOH)₂ | 1 | 146–149.5 | 62.21 / 62.19 | 6.71 / 6.68 | 3.46 / 3.50 |
| 23 | H | 2'-CH₃ | CH₃ | H | —O— | 4 | HCl | 1 | 112–115 | 67.17 / 67.34 | 7.52 / 7.74 | 4.35 / 4.10 |
| 24 | H | 2'-CH₃ | CH₃ | H | —O— | 3 | HCl | 1 | 126–128 | 66.30 / 66.21 | 7.21 / 7.30 | 4.56 / 4.51 |
| 25 | H | 2'-CH₃ | CH₃ | CH₃ | —O— | 3 | HCl | 1 | 149 | 67.41 / 67.31 | 7.51 / 7.49 | 4.35 / 4.29 |
| 26 | H | 2'-CH₃ | CH₃ | H | —O— | 5 | HCl | 1 | 115 | 68.32 / 68.24 | 7.24 / 7.13 | 4.19 / 4.21 |
| 27 | H | 2'-CH₃ | CH₃ | CH₃ | —O— | 5 | HCl | 1 | powder | 69.02 / 68.97 | 7.53 / 7.25 | 4.03 / 3.92 |
| 28 | H | 2'-CH₃ | C₂H₅ | H | —O— | 3 | HCl | 1 | 110–112 | 67.14 / 67.00 | 7.51 / 7.51 | 4.35 / 4.28 |
| 29 | H | 2'-CH₃ | C₂H₅ | C₂H₅ | —O— | 3 | HCl | 1 | 127–130 | 68.63 / 68.45 | 8.06 / 8.00 | 4.00 / 4.00 |
| 30 | H | 2'-CH₃ | —CH₂CH₂CH₂CH₂— | | —O— | 3 | HCl | 2 | 143–149 | 69.02 / 68.81 | 7.53 / 7.40 | 4.03 / 3.89 |
| 31 | H | 2'-CH₃ | —CH₂CH₂OCH₂CH₂— | | —O— | 3 | HCl | 2 | 160–164 | 65.99 / 65.89 | 7.20 / 7.20 | 3.85 / 3.85 |

The following compounds are prepared in a similar manner:
2-(5-methylaminopentyloxy)-2'-hydroxydiphenylmethane
2-(4-morpholinobutoxy)-2'-ethoxydiphenyl ether
2-(4-methylaminobutoxy)-2'-methoxydiphenyl sulfide
2-(4-methylaminobutoxy)-5-methylbiphenyl
2-(4-methylaminobutoxy)-2'-hydroxydiphenylmethylmethane
2-(5-methylaminopentyloxy)-2'-ethoxydiphenyl ether
2-4-(4-methyl-1-piperazinyl)butoxy-5-methyldiphenylmethane
2-(4-ethylaminobutoxy)-2'-hydroxydiphenylmethane
2-(4-ethylaminobutoxy)-2'-ethoxydiphenyl ether
2-(4-methylaminobutoxy)-3,5-dimethyl-2',3'-dimethoxydiphenylmethane
2-(4-methylaminobutoxy)-3-methyl-5,4'-dichlorodiphenylmethane
2-(4-methylaminobutoxy)-5-chloro-3-isopropyl-6-methyldiphenylmethane
2-(4-methylaminobutoxy)-4'-bromo-4,6-dimethyldiphenylmethane
2-(4-methylaminobutoxy)-3,4'-dimethyldiphenyl ether
2-(4-methylaminobutoxy)-4'-chlorodiphenyl ether 2-(4-methylaminobutoxy)-3,5-dibromobiphenyl
2-(4-methylaminobutoxy)-3,5,4'-tribromobiphenyl
2-(4-methylaminobutoxy)-3,5-dimethylbiphenyl
2-(4-methylaminobutoxy)-3-ethylbiphenyl

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A method for palliating conditions of depression in warm-blooded animals which comprises administering to said animal an antidepressant effective amount of a compound of the formula (II):

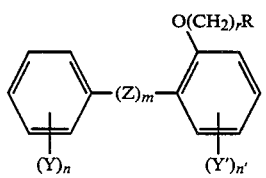

wherein R is (1)

wherein $R_1$ and $R_2$ which are alike or different are selected from the group consisting of hydrogen, $C_1$–$C_5$ alkyl and $C_1$–$C_5$ hydroxyalkyl or (2) $C_3$–$C_7$ N,N-polymethyleneiminyl, morpholino, thiomorpholino, 4-oxothiomorpholino, 1-piperazinyl, 4-methyl-1-piperazinyl, 4-ethyl-1-piperazinyl or 4-acetyl-1-piperazinyl; Y and Y' which are alike or different are selected from the group consisting of hydrogen, halo, hydroxy, trifluoromethyl, $C_1$–$C_5$ alkyl or $C_1$–$C_5$ alkoxy with the proviso that both Y and Y' are not hydrogen; Z is oxy, thio, methylene, monosubstituted methylen

wherein $R_3$ is $C_1$–$C_5$ alkyl, or disubstituted methylene

wherein $R_4$ and $R_5$ are $C_1$–$C_5$ alkyl; r is an integer of 3, 4 or 5; m is 1; n is an integer of 1 to 5; and n' is an integer of 1 to 4, or the acid addition salts thereof.

2. The method of claim 1, wherein R is amino, $C_1$–$C_3$ alkylamino, $C_2$–$C_6$ dialkylamino, $C_1$–$C_3$ hydroxyalkylamino, $C_2$–$C_6$ bis(hydroxyalkyl)amino, $C_2$–$C_6$ N-alkyl-N-hydroxyalkylamino or 1-pyrrolidinyl; Y and Y' are selected from the group consisting of hydrogen, halo, hydroxy, trifluoromethyl, $C_1$–$C_3$ alkyl or $C_1$–$C_3$ alkoxy; Z is oxy, thio, methylene or methylmethylene

n is an integer of 1 to 2; and n' is an integer of 1 or 2.

3. The method of claim 2, wherein r is 3 or 4.

4. The method of claim 2, wherein R is methylamino, ethylamino, dimethylamino, diethylamino, bis(2-hydroxyethyl)amino or 1-pyrrolidinyl; Y and Y' are selected from the group consisting of hydrogen, chloro, hydroxy, methyl, methoxy and ethoxy; Z is oxy or methylene; r is 3 or 4; m is 1; n is 1; and n' is 1.

5. The method of claim 4, wherein the compound is 2-(4-methylaminobutoxy)-3-methyldiphenylmethane.

6. The method of claim 4 wherein the compound is 2-(4-dimethylaminobutoxy)-3-methyldiphenylmethane.

7. The method of claim 4 wherein the compound is 2-(4-dimethylaminobutoxy)-5-methyldiphenylmethane.

8. The method of claim 4 wherein the compound is 2-(4-methylaminobutoxy)-2'-methoxydiphenylmethane.

9. The method of claim 4 wherein the compound is 2-(4-methylaminobutoxy)-2'-hydroxydiphenylmethane.

10. The method of claim 4 wherein the compound is 2-(4-dimethylaminobutoxy)-2'-hydroxydiphenylmethane.

11. The method of claim 4 wherein the compound is 2-(4-methylaminobutoxy)-2'-ethoxydiphenylmethane.

12. The method of claim 4 wherein the compound 2-(4-methylaminobutoxy)-2'-methyldiphenylmethane.

13. The method of claim 4 wherein the compound is 2-(3-methylaminopropoxy)-2'-methyldiphenyl ether.

14. The method of claim 4 wherein the compound is 2-(3-dimethylaminopropoxy)-2'-methyldiphenyl ether.

15. An antidepressant composition which comprises an antidepressant effective amount of a compound of claim 1 and a pharmaceutically acceptable carrier.

* * * * *